US005893368A

United States Patent [19]

Sugerman

[11] Patent Number: 5,893,368

[45] Date of Patent: Apr. 13, 1999

[54] METHOD FOR LOWERING ABDOMINAL PRESSURE

[75] Inventor: Harvey J. Sugerman, Richmond, Va.

[73] Assignee: Virginia Commonwealth University, Richmond, Va.

[21] Appl. No.: 08/648,508

[22] Filed: May 15, 1996

[51] Int. Cl.$^{6}$ .......... A61B 19/00

[52] U.S. Cl. .......... 128/898; 601/11; 606/119

[58] Field of Search .......... 606/119–126; 128/898; 601/6, 11, 45, 43, 44

[56] References Cited

U.S. PATENT DOCUMENTS

| | | | |
|---|---|---|---|
| 230,351 | 7/1880 | Seyberlich | 601/6 |
| 1,498,430 | 6/1924 | Doerfler | 601/11 |
| 2,490,395 | 12/1949 | Wilm | 601/44 |
| 2,597,637 | 5/1952 | Heidenwolf | 601/45 |
| 2,917,050 | 12/1959 | Kenyon | 606/123 |
| 3,062,215 | 11/1962 | Heyns | 606/123 |
| 3,988,793 | 11/1976 | Abitbol | 601/11 |
| 4,014,344 | 3/1977 | Gutierrez | 606/123 |

OTHER PUBLICATIONS

Heyns, Abdominal Decompression in the First Stage of Labour; Journal of Obstetrics and Gynaecology; vol. 66, pp. 220–228, 1959.

Heyns, et al., Influence of Abdominal Decompression on Intra–Amniotic Pressue and Fetal Oxygenation; The Lancet; Feb. 10, 1962, pp. 289–292.

Blecher, et al., Treatment of the Toxemias of Pregnancy; The Lancet; Sep. 23, 1967, pp. 621–625.

Coxon, et al., The Effects of Abdominal Decompression on Vascular Haemodynamics in Pregnancy; The Journal of Obstetrics and Gynaecology of the British Commonwealth, vol. 78, pp. 49–54, 1971.

MacRae, et al., Clinical and Endocrinological Aspects of Dysmaturity and the use of Intermittent abdominal decompression; The Journal of Obstetrics and Gynaecology of the British Commonwealth; vol. 78, pp. 636–641, Jul., 1971.

Varma, et al., The Effects of Abdominal Decompression on Pregnancy Complicated by the Small–For–Dates Fetus; The Journal of Obstetrics and Gynaecology of the British Commonwealth, vol.80, pp. 1086–1094, Dec., 1973.

Hofmeyr, et al., Abdominal Decompression: new data from a previous study; British Journal of Obstetrics and Gynnaecology; vol. 97, pp. 547–548; Jun., 1990.

Hofmeyr, Abdominal Decompression During Pregnancy; Effective Care in Pregnancy and Childbirth, pp. 647–652; 1989.

Hofmeyr, et al., Should Abdominal Decompression by Consigned to the History Books?, British Journal of Obstetrics and Gynaecology, vol. 97, pp. 467–469, Jun., 1990.

Shimonovitz, et al., Intermittent Abdominal Decompression: an Option for Prevention of Intrauterine Growth Retardation, British Journal of Obstetrics And Gynaecology, vol. 99, pp. 693–695, Aug., 1992.

Quinn, et al., Abdominal Decompression During the First Stage of Labour; American Journal of Obstetrics and Gynecology; vol. 83, No. 4 pp. 458–463, Feb., 1962.

Quinn, et al.,Experiences With Abdominal Decompression During Labour; American Journal of Obstetricsand Gynecology, vol. 71, No. 6, pp. 934–939, Dec., 1964.

*Primary Examiner*—Mickey Yu
*Assistant Examiner*—Kelly O'Hara
*Attorney, Agent, or Firm*—Whitham, Curtis & Whitham

[57] ABSTRACT

An abdominal decompression apparatus is used to treat a variety of disorders including acute abdominal compartment syndrome, increased intra-abdominal pressure related morbidity in severely obese persons, and pre-eclampsia and other complications associated with increased abdominal pressure in pregnancy. The abdominal decompression apparatus is worn for an extended period of time (e.g., 6–12 hours at a time), with relatively low levels of pressure being applied (e.g., –20 to –45 mm Hg). Preferably, abdominal decompression is performed on a continuous basis with the final pressure being gradually achieved. In a preferred embodiment, the patient's urinary bladder pressure is used as a measure of intra-abdominal pressure. The sensed urinary bladder pressure can be used to gauge the effectiveness of treatment as well as to control parameters of the abdominal decompression device (e.g., time of use, pressure utilized, etc.).

4 Claims, 2 Drawing Sheets

METHOD FOR LOWERING ABDOMINAL PRESSURE

BACKGROUND OF THE INVENTION

1. Field of the Invention

The invention is generally related to medical devices used for lowering intra-abdominal pressure (IAP) in patients.

2. Description of the Prior Art

Abdominal decompression has been investigated for a number of years in connection with the treatment of pregnant women. Specifically, studies have been conducted to evaluate the ability of abdominal decompression to ease the pain of labor, to increase intra-uterine fetal growth, or treat toxemia of pregnancy. In all previous investigations, abdominal decompression was performed intermittently at high negative pressures for short periods of time (e.g., −70 mm Hg for 30 seconds every minute for 30 minutes, twice daily).

Heyns, *Obstet. Gynaecol. Br. Commonw.*, 66:220–228, 1959, discloses a study wherein intermittent abdominal decompression is used for the treatment of labor pains during the first stage of labor. Eight patients were used in the study, and the patients controlled the negative pressure themselves by placing a finger over a vent tube to bring the pressure down to around 50 mm Hg in most instances for about sixty seconds. However, in some cases the pressure was brought down to as low as 150 mm Hg. The article reports that the labor pains were relieved in all eight patients, and that the treatment did not interfere with diagnosing the second stage of labor (actual commencement of delivery).

Heyns et al., *Lancet*, 1:289–292 (1962), present data from a study using intermittent abdominal decompression for thirty minutes on twelve or more occasions in 350 caucasion women during the last two months of pregnancy and during labor. In the study, amniotic fluid pressure was measured and it was found that this pressure rose to 40 mm Hg during early labor, and 50–70 mm Hg during mid-labor as the second stage approached. It was found that abdominal decompression lowered these pressures to zero or less at the height of a uterine contraction. The highest pressures were found in the small primigravida with a tight belly wall and in active athletes. The fetal heartbeat did not change in rate during uterine contractions with decompression. The placenta from women treated with decompression was reported to have a richer arteriolar and capillary network. In a non-randomized study, the perinatal death rate in babies subjected to decompression was 0.6%, compared to 3% to a non-treated group. The authors concluded that the data suggests that decompression improves fetal oxygenation.

There have been two other studies using intermittent abdominal decompression for the first stage of labor by Quin, L J et al, which are found in *Amer. J. Obstet. Gynecol.* 83:458, 1962, and *J. Obstet. Gynaecol.* 71:934, 1964. The device was used in 100 primiparas and 42 multiparas in the first study and 302 primiparas and 188 multiparas in the second study, and there was an 86% excellent or good pain relief response with its use. The device was modified with a switch to the vacuum pump which the patient activated at the onset of labor pain and turned off at the completion of a contraction. This device was manufactured by the J. H. Emerson Co., Cambridge, Mass., and called the "Birtheez".

Blecher et al., *Lancet*, 2:621–625, 1967, reports on a study with fifty caucasion and 80 non-white patients treated by abdominal decompression applied for ten minutes twice on the first day of treatment, twenty minutes twice on the second day of treatment, and thirty minutes twice on the third and subsequent days of treatment. Toxemia of pregnancy was hypothesized to be secondary to uterine ischemia produced by increased IAP, and that abdominal decompression would prevent this ischemia and prevent or correct toxemia. The pressures used in the study were individually gauged according to the patients' tolerance, and were generally between −50 and −80 mm Hg for 15 seconds in every ½ minute. It was reported that the treated patients whose hypertension was secondary to toxemia had a significantly better response, and that they had a significantly better fetal survival rate.

Coxon et al., *J. Obstet. Gynaecol. Br. Commonw.*, 78:49–54, 1971, reports on a study wherein the authors used the radioisotope indium 113 m bound to transferrin and an external counter and observed a 30% increase in placental count rate with abdominal decompression. The use of abdominal decompression during a uterine contraction in the first stage of labor resulted in a 15% increase in placental site count rate over the uterine wall away from the placental site. The authors apparently used test conditions where approximately −70 mm Hg abdominal decompression was applied, but the frequency and duration were not provided. The Coxon et al. study appears to support the Heyns hypothesis that abdominal decompression improves fetal blood flow.

Macrae et al., *J. Obstet. Gynaecol. Pr. Commonw.*, 78:636–641. 1971, reports on a study where intermittent abdominal decompression (negative pressure of −70 mm Hg applied for fifteen seconds of every minute over a ½ hour period, with treatment sessions ranging from 2–3 times per week) was asserted to raise estriol levels to normal. Dysmaturity, which is associated with a high perinatal mortality, is associated with decreased estriol levels.

Varma et al., *J. Obstet. Gynaedol Br. Commonw.*, 80:1086–1094, 1973, studied intermittent abdominal decompression in 70 pregnant patients with "small-for-dates" fetuses as compared to 70 similar control cases. The decompression group received abdominal decompression once a day in the Heyns decompression suit in which they were placed for thirty minutes using a negative pressure of 80–90 mm Hg for 25 seconds every minute. Ultrasound cephalometry and 24-Hr urinary estrogen levels were measured. The mean fetal growth rate of the decompression group was significantly greater than the untreated group and was associated with a significantly higher estrogen excretion and lower incidence of fetal distress as well as a significantly higher Apgar score and a lower percent of low birth weight babies and perinatal mortality.

Hofmeyr, "Abdominal decompression during pregnancy", in *Effective Care in Pregnancy and Childbirth*, Chalmers I, Enkin M, Keirse M J N C, eds., Oxford University Press, Oxford, 1989, pp. 647–652, provides a review of the literature on abdominal decompression and describes the apparatus, the technique, and indications for its use. However, it is concluded that: "There is some evidence that abdominal decompression may be of value in certain abnormal states of pregnancy but the studies reported to date are not of sufficient methodological quality to support the use of abdominal decompression except within the context of further methodologically sound, controlled trials. Nevertheless, there are so few options for managing the compromised fetus other than elective delivery that it is important to subject abdominal decompression to further evaluation."Hoffmeyr et al., *Br. J. Obstet Gynaecol.*, 97:547–548, 1990, provided a further evaluation of a previous randomized controlled trial designed to test the hypothesis that higher developmental quotients would develop in infants born to mothers treated with intermittent abdominal decompression secondary to improved fetal blood flow. The patients were randomized to treatment or control groups, and the treated group received abdominal decompression three times per week from thirty weeks of gestation using patient controlled decompression for fifteen seconds each minute over thirty minutes. No differences in gestation time, birthweight at delivery or one minute Apgar scores were noted between the groups.

In an editorial, Hofmeyr, *Br. J. Obstet. Gynaecol.*, 97:467–469, 1990, suggests that the negative reaction to the failure of abdominal decompression to improve fetal development scores or intelligence quotients in normal pregnancies, as initially suggested by Heyns, may detract from its possible benefits to decrease the pain of labor and fetal distress, or treat toxemia or poor fetal growth which may be secondary to impaired placental blood flow.

Shimonovitz et al., *Br. J. Obstet. Gynaecol.*, 99:693–695, 1992, describe three women with a "bad obstetric history", e.g., multiple recurrences of toxemia, severe intrauterine growth retardation, and fetal death, who were treated with intermittent abdominal decompression (−70 mm Hg for thirty seconds every minute for thirty minutes, two times a day) with excellent results including correction of hypertension and improved fetal growth.

SUMMARY OF THE INVENTION

It is an object of this invention to provide a method and apparatus for lowering intra-abdominal pressure which can be used in the treatment of a wide variety of disorders such as those which are associated with acute abdominal compartment syndrome, increased intra-abdominal pressure related morbidity in severely obese individuals, and pre-eclampsia of pregnancy.

It is another object of this invention to provide a method and apparatus for lowering intra-abdominal pressure which provides relatively low levels of negative pressure (e.g., −20 to −45 mm Hg) to a patient's abdomen, on a continuous basis, for extended periods of time.

It is yet another object of this invention to provide a method and apparatus for lowering intra-abdominal pressure in a patient that utilizes urinary bladder pressure measurements of the patient to control intensity and treatment duration.

According to the invention, a patient's intra-abdominal pressure is advantageously lowered by providing abdominal decompression to the patient on a continuous basis for an extended period of time. The abdominal decompression device can be constructed in a variety of forms with the principal object being to apply negative pressure at the site of the patient's chest and abdomen. The abdominal decompression device will preferably either have an air tight suit positioned over a rigid frame which is spaced slightly (e.g., 2–6 inches) away from the patient's chest and abdomen; or, alternatively, will include a rigid dome vest made of plastic or other suitable materials which will be held in place on the patient's chest and abdomen. In the case of a rigid dome vest, a material which traverses around the patient's back that is connected using clips or hook and loop connecters (Velcro®) or other suitable connectors can be used to hold the dome in place.

A pump is connected to the air tight suit or dome vest and is used to apply negative pressure in the space between the suit or vest and the patient. A guage is connected to the line connected to the pump for aiding in regulating the vacuum pressure inside the abdominal decompression device.

It has been observed that a failing of prior abdominal decompression devices is that the pressure is often too high to be comfortable (e.g., 100–150 mm Hg), and is often not regulated (e.g., patient applied finger on a vent tube). The method and apparatus of this invention is directed to providing a low vacuum pressure (e.g., 20–45 mm Hg) which can be tolerated by a patient for an extended period of time. Preferably, the abdominal decompression device will be worn for six to twelve hours, and most preferably overnight for eight hours while the patient is sleeping. In addition, unlike prior art devices, the method and apparatus of this invention contemplates the application of continuous, as opposed to intermittent, negative pressure on the patient's chest and abdomen. The prolonged, continuous, low negative pressure treatment provides a more reliable mechanism for reducing intra-abdominal pressure than prior devices which rely on high pressures for intermittent time periods.

Another failing of prior art abdominal decompression devices is that they do not provide any means of determining the intraabdominal pressure of the patient during treatment. The method and apparatus of this invention contemplate using the patient's urinary bladder pressure as an assessment of intraabdominal pressure. It has been found that in most clinical situations urinary bladder pressure accurately reflects intraabdominal pressure. The urinary bladder pressure measurement can be determined using a Foley catheter or other suitable device, and would preferably be left in place during the initial application of vacuum pressure to the patient's chest and abdomen.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1A:
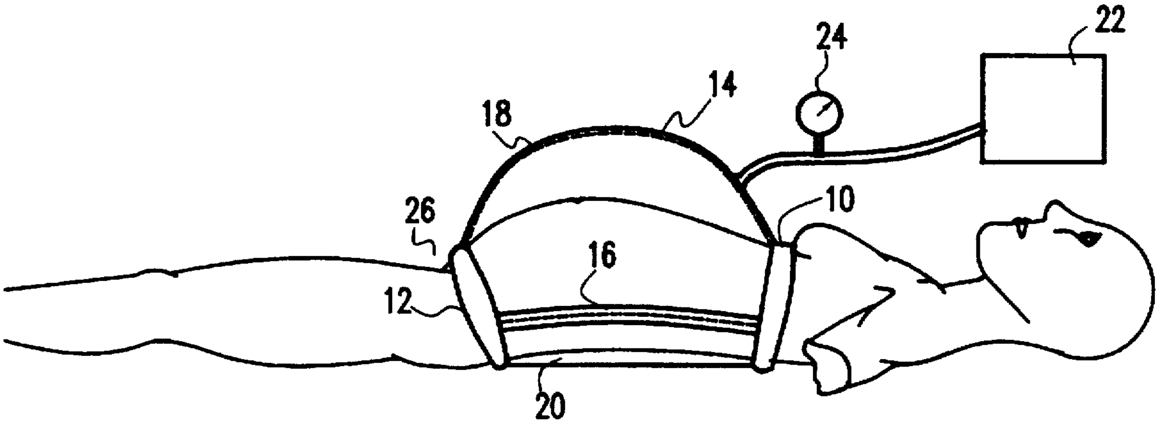
FIGS. 1*a* and 1*b* show side and top schematic views of a patient positioned in an abdominal decompression device of the present invention.

Clinical and animal studies have demonstrated that increased intraabdominal pressure (IAP) produces elevated renal venous and inferior vena caval pressure, and these conditions cause the kidneys to leak protein and to produce hormones which increase systemic blood pressure. The increased IAP also pushes the diaphragm cephalad, "squeezing" the lungs, interfering with respiratory function, and raising intra-thoracic pressure. This impairs venous return from the brain, raising intracranial pressure, as well as impairs return from the liver, interfering with the intestinal venous drainage and causing liver vascular engorgement, leading to the risk of hepatic rupture in the case of eclampsia.

Lowering IAP can be useful for the treatment of pre-eclampsia and toxemia of pregnancy, decreasing the pain of labor, and improving intra-uterine fetal growth. However, for more effective treatment than has been achieved with previous investigative devices, a more gradual decrease in negative pressure is required. This allows the pressure reducing device to be more easily tolerated by the patient and to be "worn" or "used" for extended periods of time (e.g., 6–12 hours, such as eight hours overnight while sleeping). The prolonged treatment provides a significantly enhanced effect on lowering IAP, not heretofore observed in previous investigations.

Furthermore, the method and apparatus of this invention can be used for treating a number of different conditions. For example, increased IAP in severely obese individuals can result in obesity hypoventilation syndrome, chronic venous stasis ulcers or edema (e.g., lower extremity), idiopathic intracranial hypertension (pseudotumor cerebri), systemic hypertension secondary to obesity, nephrotic syndrome of obesity, and gastro-esophageal reflux. These disorders which stem from the patient's obese condition can be treated or alleviated with a prescribed program for reducing IAP. In addition, "Acute Abdominal Compartment Syndrome" is often seen in critically ill medical or surgical patients where there is an acute increase in IAP, and this syndrome may cause kidney and lung failure, infarction of the intestine, or marked increases in brain cerebrospinal fluid pressure. Patients suffering from acute abdominal compartment syndrome should benefit from applying a negative pressure continuously in the intensive care unit or other treatment setting for as long as the IAP is elevated.

Those skilled in the art will recognize that other disorders stemming from or associated with elevated IAP would benefit from a program and device designed to reduce IAP to normal levels. For example, the method and apparatus of this invention may also be useful in the treatment of obesity related Type II diabetes mellitus and sleep apnea syndrome.

In a preferred embodiment of this invention, the urinary bladder pressure is utilized to estimate and monitor changes in IAP. It has been found that urinary bladder pressure measurements accurately reflect IAP in most clinical situations. Studies have shown that the average urinary bladder pressure in morbidly obese patients is 18±0.7 (range 12 to 42) cm $H_2O$, while non-obese patients have a urinary bladder pressure of 7.1±1.6 cm $H_2O$. In addition, clinical studies have shown that the urinary bladder pressure is between 20–30 cm $H_2O$ during the third trimester of pregnancy. The apparatus of this invention would be used to apply negative pressure on the patient's abdomen until such time as the urinary bladder pressure measurements are more closely associated with those found in non-obese patients (e.g., 10–14 cm $H_2O$). Preferably the target urinary bladder pressure measurement would be selectable by the physician, and would be chosen to be clinically effective for the condition or syndrome being treated. By using bladder pressure measurements of the patient under treatment to control the intensity and duration of treatment with the negative pressure device, the IAP of the patient can be continuously monitored during treatment without the need for intermittent breaks in negative pressure to evaluate IAP by other means.

Figure 1B:
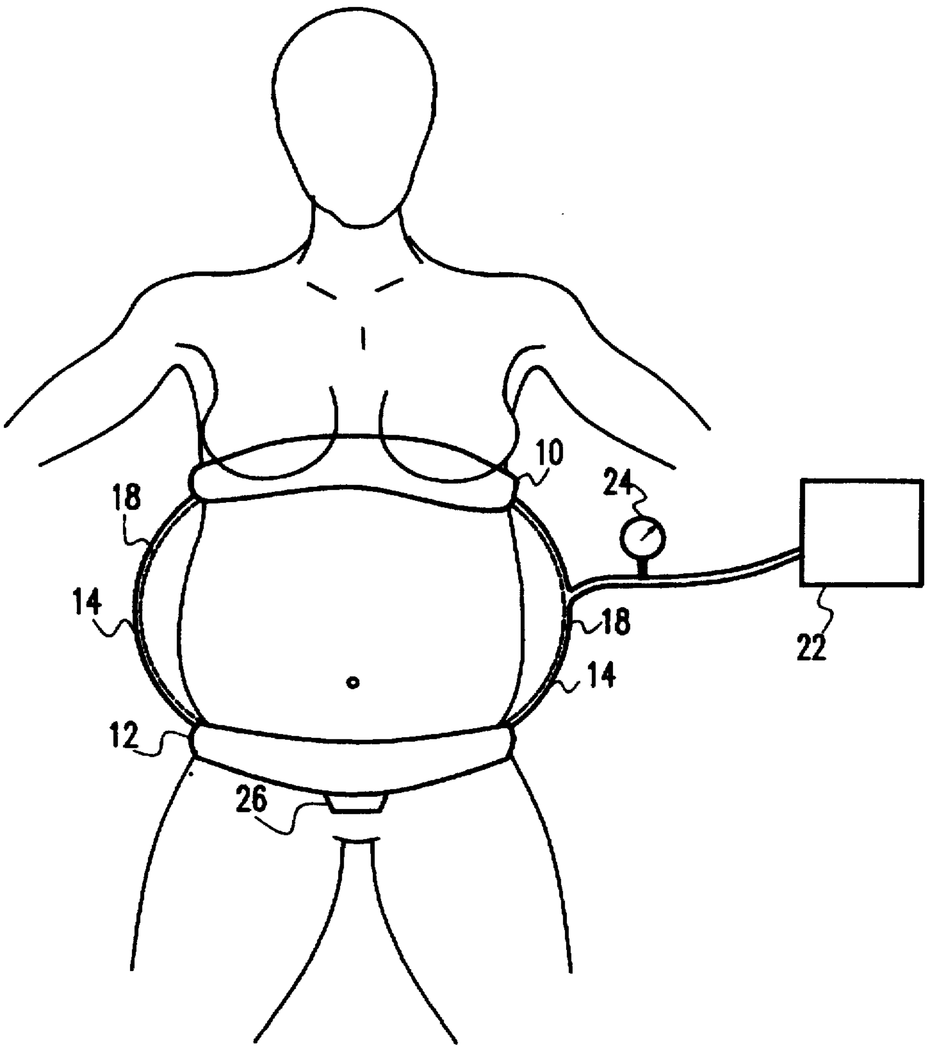

FIGS. 1*a* and 1*b* schematically show one example of an abdominal decompression system according to the present invention. Inflatable cuffs 10 and 12 are secured at the chest and pelvis of the patient being treated. Cuffs 10 and 12 are intended to maintain an air tight enclosure; therefore, body contacting surfaces may be provided with features intended to promote air tight connections. For example, silicone oil may be applied and held within recessed regions (not shown) on the body contacting surfaces of the cuffs 10 and 12, or the body contacting surfaces of the cuffs 10 and 12 could include pocket regions designed to prevent ambient air from being suctioned under the cuffs 10 and 12. While the preferred abdominal decompression device utilizes inflatable cuffs 10 and 12 because of the advantages of being lightweight and conformable to the contours of the patient's body, other materials such as neoprene rubber or the like might be used for the cuffs 10 and 12. Or even more simply, a drawstring can by used to cinch the material around the patient's chest and pelvis.

Furthermore, while FIGS. 1*a*–*b* show a cuff 12 placed at the pelvis, it should be understood that the abdominal decompression device could be "sack-shaped", including only one cuff 10 positioned at the patient's chest and extending therefrom to cover the wearer's legs.

An air tight enclosure 14 is positioned between cuffs 10 and 12. The air tight enclosure 14 can be made of plastic, nylon®, goretex®, or other suitable materials. In the case of a single cuff 10 design, the air tight enclosure 14 would extend over the patient's legs and feet. An air tight zipper 16 could be provided for easier patient access into the abdominal decompression device. Alternatively, a non-zippered overlap enclosure could be provided which self-seals with the application of negative pressure.

A frame with multiple perforations 18, preferably made of metal, plastic, or other rigid materials is positioned under the air tight enclosure 14 and is used to support the air tight enclosure slightly above the patient's chest and abdomen, but suffient to provide access for the application of negative pressure. A preferred distance for the frame 18 to hold the enclosure 14 above the patient's chest and abdomen is two to six inches. The frame 18 may advantageously encircle three quarters of the patient's body and be positioned on the mattress of a bed or be affixed to a back support 20 on which the patient rests during treatment. The back support can be made from any suitable material and should provide the patient with comfort during extended periods of wear either in bed or in a chair.

Negative pressure is applied in the space between the frame 18 and the abdomen using a vacuum source 22. The air tight enclosure 14 on top of the frame 18 allows the negative pressure environment around the patient's chest and abdomen to be generated by the vacuum source 22. The vacuum source could be a variable vacuum pump, an AC pump or a DC pump, or any other suitable device which can evacuate air from between the frame 18 and patient's chest and abdomen. A pressure guage 24 is provided to monitor the negative pressure being applied. In the preferred embodiment of this invention, a constant negative pressure of approximately −20 to −45 mm Hg is exerted by vacuum source 22, and the pressure is applied continuously for an extended treatment period. In most cases, it is anticipated that the treatment period will be six to twelve hours (e.g., approximately eight hours overnight); however, it should be understood for certain conditions longer or shorter periods might be more clinically appropriate. In addition, the amount of negative pressure is ideally low (e.g., −20 to −45 mm Hg in most applications) since higher negative pressures are generally uncomfortable to patients for extended periods of time; however, for certain conditions, higher or lower pressures may be useful for clinical effectiveness.

Figure 2A:
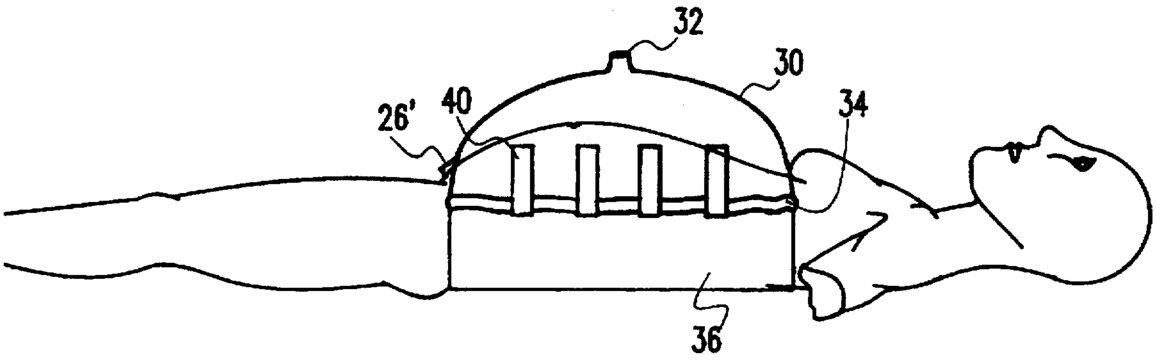
FIG. 2*a* and 2*b* show side and top schematic views of a domed vest for abdominal decompression according to the present invention.
Figure 2B:
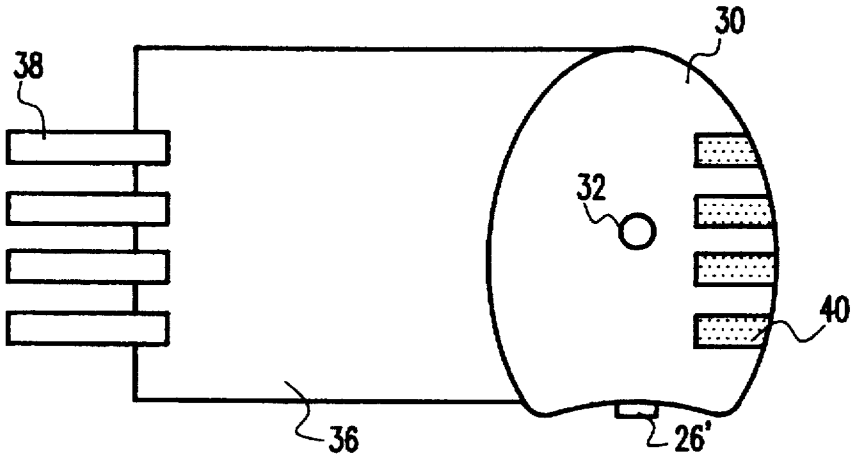

FIGS. 2*a* and 2*b* show an alternative design for the abdominal decompression device according to the present invention. In FIGS. 2*a* and 2*b*, a rigid dome 30 is placed over the patient's chest and abdomen. The dome 30 extends above the patient and defines a cavity which can be used to apply negative pressure to the patient's chest and abdoment. Vacuum pressure is applied to the cavity through port 32. The dome 30 can be made of a plastic or metal material, and should be of sufficient rigidity to withstand deforming under the pressure of the applied vacuum (e.g., preferably −20 to −45 mmHg as discussed above in connection with FIGS. 1*a* and 1*b*). An air tight seal 34, such as a rubber gasket or other suitable material, will seal the dome 30 against the patient's chest and abdomen. The dome 30 will be held in place using an attached posterior vest 36 which extends from one side of the dome 30 around the patient's back and is connected to the opposite side of the dome 30 using connectors 38 and 40, which may be Velcro® strips, clips, tape, straps with punch holes for connection to a belt-type connector, or other suitable devices. The abdominal decompression device of FIGS. 2*a* and 2*b* has the advantage of enabling the patient to get in and out of the device more easily than the design shown in FIGS. 1*a* and 1*b*.

Urinary bladder pressure detection system, shown as element 26 in FIGS. 1*a–b* and element 26' in FIGS. 2*a–b*, provides measurements of the patient's urinary bladder pressure. The detection system 26 or 26' can take the form of a urinary Foley catheter or another suitable device. As discussed above, it has been found that the patient's urinary bladder pressure accurately reflects the intra-abdominal pressure of the patient being treated. The normal bladder pressure in non-obese individuals averages approximately 7 cm $H_2O$, whereas the bladder pressure is considerably elevated (e.g., 15–42 cm $H_2O$) in severely obese patients, in patients suffering from acute abdominal compartment syndrome, and in patients with complicated pregnancies.

The bladder pressure measurement should provide an effective mechanism for controlling the treatment regimen of a patient suffering from elevated IAP in a number of different situations. For example, in critically ill patients suffering from the acute abdominal compartment syndrome, the abdominal decompression device can be fitted onto the patient and the duration of the negative pressure and amount of negative pressure applied can be controlled in a manner which achieves a pre-selected level of bladder pressure. That is, treatment continues until halted by a physician or the pre-selected level is reached. In severely obese patients or in pregnant patients, a pre-selected time of negative pressure application can be used, with the bladder pressure measurements providing feedback on the effectiveness of the treatment.

EXAMPLE 1

Pigs weighing approximately 70 kg have been studied using an abdominal decompression device similar to that shown in FIGS. 1*a–b*, which has been named an "ABOVAC" which is an acronym for abdominal vacuum, following experimentally induced increased intra-abdominal pressure and volume re-expansion. Pigs weighing approximately 70 kg were anesthetized and underwent an infusion of a polyethylene glycol solution (Go-Lytely) into their abdomen in order to increase their intra-abdominal pressure (IAP), as measured by urinary bladder pressure, to 25 mm Hg above baseline. This increased IAP was maintained for three hours. The normal fall in cardiac index associated with this increase in IAP was prevented by increasing the intravascular volume with Lactated Ringer's solution, in an attempt to mimic a chronic, compensated state of increased IAP as seen in both severe obesity and pre-eclampsia. The increased IAP and volume expansion was associated with a significant ($p<0.01$) increase in mean systemic arterial pressure, from 91±4 to 126±3 mm Hg. Application of the ABOVAC device at a pressure of −40 mm Hg for four hours was associated with a 12 mm Hg decrease ($p<0.01$) in IAP and fall ($p<0.01$) in mean systemic arterial pressure to 101±23 mm Hg. The increased IAP was also associated with an increase ($P<0.01$) in intracranial pressure from 11±0.8 to 21±1.9 mm Hg; this decreased ($p<0.01$) to 15±0.8 mm Hg following application of the ABOVAC. Significant increases in central venous and femoral venous pressures were also noted with the increased IAP which also fell significantly with the use of the ABOVAC. The effects of the ABOVAC were noted immediately after it was turned on and remained effective throughout the four hour period of its application.

These data suggest that an increased IAP is responsible for systemic hypertension, chronic lower extremity venous stasis, and intracranial hypertension seen in both severe obesity and pre-eclampsia and that an ABOVAC device which lowers IAP will probably be of significant clinical benefit in both of these conditions, as well as the acute abdominal compartment syndrome seen in some critically ill patients.

EXAMPLE 2

Five severely obese patients with systemic hypertension have been studied in the ABOVAC using a poncho arrangement with a cage placed within it (similar to FIGS. 1*a–b*). Four patients were in the device for six hours and one for three hours. All five patients stated that they felt much less short of breath in the ABOVAC. The patients' urinary bladder pressure was 22.6±2.4 in $H_2O$, range 19 to 28 cm $H_2O$ (where normal is 7) prior to use of the ABOVAC. The negative applied pressure ranged from 20–35 mm Hg. In four of the five patients, urinary bladder pressures fell by 4–8 cm $H_2O$. The mean decline was to 16.9±4.2 in $H_2O$. Systemic blood pressure did not change, but the drop in abdominal pressure (as reflected in bladder pressure) was associated with an increase in urine output and urinary sodium excretion (naturesis) in each of the four patients in whom urinary bladder pressure fell. The mean change in urinary sodium was from 85±42 to 121±40 in Eq/hr during the ABOVAC which fell to 71±30 Eq/hr when the ABOVAC was turned off for all patients. These data are consistent with an increased venous return to the heart, decreased intra-abdominal pressure, and decreased intra-pleural pressure.

The one patient who had no change in urinary bladder pressure also had no increase in urinary sodium excretion. At the time of surgery, this patient's subcutaneous tissue measured 12 cm; whereas, the patients who responded had subcutaneous tissue measurements of 6–9 cm. Thus, it is likely that the patient whose bladder pressure failed to respond had a much heavier abdominal wall which would have required a stronger vacuum pump to lower this pressure.

It is expected that use of the ABOVAC through the night (e.g., approximately eight hours) would result in a significant decrease in intra-vascular volume which would lead to a decrease in systemic as well as pulmonary artery blood pressures. It should also improve arterial blood gases, as a reflection of improved pulmonary function.

EXAMPLE 3

One patient has been studied in the ABOVAC shell-type device shown in FIGS. 2*a–b*. This was much more comfortable for the patient and easier to apply. Because of a good vacuum seal, no retention straps were required. There was an excellent effect on bladder pressure which was decreased from 23 cm $H_2O$ to 6 cm $H_2O$ with only −21 mm Hg pressure. Lower bladder pressures could have been achieved with only minor increases in vacuum negative pressures, emphasizing the importance of monitoring bladder pressures with the device. The study patient had obesity hypoventilation syndrome. Pre-ABOVAC arterial blood gases were $PaO_2$ 76 mm Hg; $PaCO_2$ 49 mm Hg. Blood gases after 2.5 hours in the ABOVAC were $PaO_2$ 81 mm Hg; $PaCO_2$ 44 mm Hg, which is a significant improvement over a short period of time. At six hours the $PaCO_2$ had fallen further to 41 mm Hg. His means systemic arterial pressure fell from 98 mm Hg to 78 mm Hg shortly after the ABOVAC was turned on and remained at that level throughout it six hours of use. There was a decrease in sonographic measured internal jugular venous cross-sectional diameter from 11 to 7 mm with an increased jugular venous flow, confirming the decreased intra-thoracic pressure with abdominal decompression and improved venous drainage from the brain. This supports its prospective use for patients with pseudotumor cerebri. The patient stated that he could breath much more comfortably and felt less bloated while in the device. This study with the shell-type device demonstrates the functionality and effectiveness of the shell-type design.

The above-studies suggest that the ABOVAC will lead to decreased intra-abdominal and pleural pressures, a decrease in intra-vascular volume, decreased systemic and pulmonary blood pressures, improved pulmonary function, decreased lower extremity venous stasis, and decreased intracranial hypertension in morbidly obese patients. Furthermore, the ABOVAC device should be of benefit to women with pre-eclampsia as well as be of a benefit to critically ill patients with increased intra-abdominal pressure as a result of an acute abdominal compartment syndrome.

While the invention has been described in terms of its preferred embodiments, those skilled in the art will recognize that the invention can be practiced with modification within the spirit and scope of the appended claims.

I claim:

1. A method for performing abdominal decompression on a patient, comprising the steps of:

enclosing a space around a patient's chest and abdomen with an air tight enclosure; and continuously applying a negative pressure to the patient's chest and abdomen for a period of six to twelve hours by withdrawing air from space around the patient's abdomen continuously for said period of six to twelve hours.

2. The method of performing abdominal decompression of claim 1 wherein said step of continuously applying a negative pressure includes the step of selecting said negative pressure to range from −20 mm Hg to −45 mm Hg.

3. A method of performing abdominal decompression on a patient, comprising the steps of:

enclosing a space around a patient's chest and abdomen;

applying a negative pressure to the patient's chest and abdomen for a pre-selected period of time by withdrawing air from said space around the patient's chest and abdomen;

measuring urinary bladder pressure of the patient; and controlling said negative pressure applied during said applying step in accordance with urinary bladder pressure measurements made during said measuring step.

4. The method of claim 3 wherein the step of measuring is performed intermittently.

* * * * *